(12) United States Patent
Ohbayashi et al.

(10) Patent No.: US 6,613,564 B2
(45) Date of Patent: Sep. 2, 2003

(54) ENZYME-PROTEIN COMPLEX

(75) Inventors: Hirokazu Ohbayashi, Tokyo (JP); Yuriko Kitano, Higashimurayama (JP)

(73) Assignee: Nichirei Corporation, Tokyo (JP)

( * ) Notice: Subject to any disclaimer, the term of this patent is extended or adjusted under 35 U.S.C. 154(b) by 300 days.

(21) Appl. No.: 09/740,903

(22) Filed: Dec. 21, 2000

(65) Prior Publication Data

US 2001/0005583 A1 Jun. 28, 2001

(30) Foreign Application Priority Data

Dec. 22, 1999 (JP) .......................... 11-365554

(51) Int. Cl.[7] .................. G01N 33/535; G12N 11/06; C07K 17/06

(52) U.S. Cl. .................. 435/345; 435/188; 435/960; 424/179.1; 530/391.1; 530/391.3; 530/391.5

(58) Field of Search .................. 424/179.1; 435/7.94, 435/188, 345, 960; 530/391.1, 391.3, 391.5

(56) References Cited

U.S. PATENT DOCUMENTS

| | | | |
|---|---|---|---|
| 5,053,520 A | 10/1991 | Bieniarz et al. | |
| 5,057,313 A | 10/1991 | Shih et al. | |
| 5,084,560 A | 1/1992 | Hellstrom et al. | |
| 5,658,741 A | 8/1997 | Bolton et al. | |
| 6,252,053 B1 * | 6/2001 | Ohbayashi et al. | 530/391.3 |

FOREIGN PATENT DOCUMENTS

| | | |
|---|---|---|
| EP | 0 122 028 | 10/1984 |
| EP | 0 123 300 | 10/1984 |
| EP | 0 151 492 | 8/1985 |
| EP | 0 155 224 | 9/1985 |
| EP | 0 269 451 | 6/1988 |
| EP | 0 992 794 A2 | 4/2000 |
| JP | 59-220199 | 12/1984 |
| JP | 63-503138 | 11/1988 |
| JP | 3-158758 | 7/1991 |
| JP | 6-509167 | 10/1994 |
| JP | 7-216000 | 8/1995 |
| JP | 10-084959 | 4/1998 |
| WO | WO 87/05031 | 8/1987 |
| WO | WO 93/01498 | 1/1993 |
| WO | WO 95/24631 | 9/1995 |
| WO | WO 97/14028 | 4/1997 |

OTHER PUBLICATIONS

K. Fujiwara, et al., Journal of Immunological Methods, vol. 110, pp. 47–53, "The Use of N-[β-(4-Diazophenyl)Ethyl] Maleimide as a Coupling Agent in the Preparation of Enzyme-Antibody Conjugates", 1988.

C. A. Rowe, et al., Anal. Chem., vol. 71, pp. 3846–3852, "Array Biosensor for Simultaneous Identification of Bacterial, Viral, and Protein Analytes", 1999.

S. S. Ghosh, et al., Bioconjugate Chem., vol. 1, pp. 71–76, "Use of maleimide-Thiol Coupling Chemistry for Efficient Syntheses of Oligonucleotide-Enzyme Conjugate Hybridization Probes," 1990.

Derwent Publications, AN 1990–286254, JP 02 201162, Aug. 9, 1990.

(List continued on next page.)

*Primary Examiner*—Long V. Le
*Assistant Examiner*—Changhwa J Cheu
(74) *Attorney, Agent, or Firm*—Oblon, Spivak, McClelland, Maier & Neustadt, P.C.

(57) ABSTRACT

The invention relates to a complex of enzyme, protein and carrier comprising two or more molecules of an enzyme conjugated through amino group or other group to a carrier such as polylysine, and a protein (for example, antibody) with a specific binding potency to other substance(s) (for example, antigen) conjugated to at least one of said two or more molecules of the enzyme, which enables accurate assay of a trace amount of a substance at a high sensitivity.

27 Claims, 1 Drawing Sheet

OTHER PUBLICATIONS

Derwent Publications, AN 1991–196013, JP 03 089165, Apr. 15, 1991.

Derwent Publications, AN 1991–153208, JP 03 089164, Apr. 15, 1991.

Derwent Publications, AN 1990–113509, JP 02 066459, Mar. 6, 1990.

Derwent Publications, AN 1986–281802, JP 61–205863, Sep. 12, 1986.

Derwent Publications, AN 1984–034233, JP 58–225028, Dec. 27, 1983.

Pierce Catalog Handbook, 13 pages, "Technical Section," 1994–1995.

A.H. Blair, et al., Journal of Immunological Methods, vol. 59, pp. 129–143, "Linkage of Cytotoxic Agents To Immunoglobulins," 1983.

R.P. Haugland, Methods in Molecular Biology, vol. 45, pp. 235–243, "Coupling of Monoclonal Antibodies with Enzymes," 1995.

E. Ishikawa, et al., Journal of Immunoassay, vol. 4, No. 3, pp. 209–327, "Enzyme–Labeling of Antibodies and Their Fragments For Enzyme Immunoassay and Immunohistochemical Staining," 1983.

S. Hashida, et al., Journal of Applied Biochemistry, vol. 6, pp. 56–63, "More Useful Maleimide Componds of The Conjugation of Fab' To Horseradish Peroxidase Through Thiol Groups in the Hinge," 1984.

P.K. Nakane, et al., The Journal of Histochemistry and Cytochemistry, vol. 14, No. 12, pp. 929–931, "Enzyme–Labeled Antibodies: Preparation and Application for the Localization of Antigens," 1967.

P.K. Nakane, et al., The Journal of Histochemistry and Cytochemistry, vol. 22, No. 12, pp. 1084–1091, "Peroxidase–Labeled Antibody A New Method of Conjugation," 1974.

Z.–R. Shi, et al., The Journal of Histochemistry and Cytochemistry, vol. 36, No. 3, pp. 317–322, "A Comparison of Three Immunoperoxidase Techniques for Antigen Detection in Colorectal Carcinoma Tissues," 1988.

R. Giorno, Diagnostic Immunology, vol. 2, pp. 161–166, "A Comparison of Two Immunoperoxidase Staining Methods Based on the Avidin–Biotin Interaction," 1984.

* cited by examiner

ENZYME-PROTEIN COMPLEX

BACK GROUND OF THE INVENTION

1. Field of the Invention

The present invention relates to a complex of enzyme, protein and carrier prepared by conjugating a protein with a specific binding potency to other substance(s) onto an enzyme covalently conjugated to a carrier and the complex is utilized for immunoassay such as immunohistochemistry and enzyme immunoassay.

2. Description of the Related Art

Owing to the recent progress in immunochemistry, immunoassay capable of detecting a trace amount of a substance at a high sensitivity by using an antigen-antibody reaction has been used widely. Currently, two fields of general types of immunoassay are immunohistostaining and enzyme immunoassay.

Immunohistostaining is means for detecting a specific antigen on a tissue with an antibody specifically recognizing the antigen. Generally, an antibody recognizing a specific antigen is subjected to a reaction on a thin section sliced from a block prepared by fixing a tissue and then embedding the tissue in paraffin; by examining the presence or absence of the reacted antibody, the presence of the antigen can be determined. The antibody allowed to first react with the antigen is generally called primary antibody. When a substance emitting a signal detectable visually or with an apparatus is conjugated to the primary antibody, the intensity of the signal indicates the amount of the primary antibody, which corresponds in turn to the amount of the antigen on the section. As the substance emitting the signal for attaining the purpose, fluorescent substance and enzyme may be mentioned. At an early development stage of immunohistostaining, fluorescent substance was used as a substance emitting such signal. In that case, fluorescent microscope was necessary for detecting fluorescence.

Subsequently, enzyme-labeled antibody method was developed by Nakane et al., which enabled the analysis of stained image with optical microscope. Currently, enzyme is generally used as a substance emitting signal. For effecting immunohistostaining, a color reaction corresponding to the activity of an enzyme if conjugated to a primary antibody can be effected by adding a chromogenic substance to the enzyme, and the color reaction corresponds to the amount of the antibody, namely the amount of the antigen present on the tissue. However, generally, a sufficient sensitivity can never be recovered by the method.

The method most commonly used currently is called streptavidin-biotin method (SAB method), namely means for amplifying the signal of a primary antibody bound to an antigen, thereby detecting the signal. The method comprises first subjecting a primary antibody recognizing a specific substance on a tissue section to reaction therewith. Then, a secondary antibody binding to the primary antibody is subjected to reaction therewith. Generally, the secondary antibody is a polyclonal antibody which recognizes and bonds to the primary antibody thereto. Accordingly, plural molecules of the secondary antibody are bound to the primary antibody. Plural molecules of biotin are preliminarily conjugated to each molecule of the secondary antibody. An enzyme-conjugated streptavidin (enzyme reagent) is allowed to react with the primary antibody-biotin-conjugated secondary antibody complex. It is known that streptavidin can strongly be bound to biotin. Therefore, a complex of primary antibody—biotin-conjugated secondary antibody—enzyme-conjugated streptavidin is formed. Because plural molecules of the biotin-conjugated secondary antibody conjugate are bound to each molecule of the primary antibody and plural molecules of the enzyme-conjugated streptavidin conjugate are bound to each molecule of the biotin-conjugated secondary antibody conjugate according to the method, consequently, the amount of the enzyme bound indirectly to the primary antibody can be increased markedly. As a result, the antigen on the tissue section can be detected at a high sensitivity.

As described previously, the SAB method is an excellent method capable of producing a more intense signal because a great many molecules of an enzyme are ultimately bound to the primary antibody bound to the antigen. However, from another standpoint of the procedures, three steps of procedures, namely reaction of primary antibody, reaction of secondary antibody, and reaction of enzyme reagent, are required to be carried out. As described previously, the SAB method includes many steps and cannot be evaluated to be satisfactory in the aspects of clinical practice and the like, demanding rapidity and simplicity along with accuracy. Thus, it is expected that the SAB method is improved.

As another means of general immunoassay, enzyme immunoassay (EIA) is known. Typical principle and procedure of EIA are as follows. First, an antibody recognizing a substance desired to be assayed is immobilized on a carrier such as polystyrene bead or microplate. After subsequently blocking the carrier with protein such as albumin, a solution (sample) containing a substance (antigen) as an intended assay object is then added. Thereafter, an antigen-recognizing antibody conjugated with an enzyme (enzyme-labeled antibody) is added. In other words, two antibodies interpose the antigen therebetween. Then, an excess of the enzyme-labeled antibody is washed off; a chromogenic substrate of the enzyme is added for color development. Because the amount of the antigen depends on the activity of the enzyme, the concentration of the antigen in the sample can be determined by comparison with the color development of a sample containing antigen at preliminarily known concentration. A number of factors are responsible for the sensitivity of enzyme immunoassay, and the quality of the enzyme-labeled antibody is one of the significant factors. More specifically, it is thought that a more intense signal can be obtained when the enzyme-labeled antibody has many molecules of the enzyme, whereby the antigen can be assayed at a high sensitivity.

As described previously, the quality of the enzyme-labeled antibody is very important for immunoassay and influences markedly the sensitivity of assay system or the number of the steps included in the procedure. As illustrated below, many attempts have been made in order to obtain an enzyme-labeled antibody that achieves a high sensitivity. Many of them comprise conjugating many molecules of an enzyme and an antibody to a carrier.

In Japanese Patent Application Publication JP-A 63–503138 (1988), an antibody was conjugated to a carrier conjugated with a derivative of a detectable label such as drug, toxin, chelator and boron adduct. As the carrier, is used aminodextran; first, a drug such as methotoxate is conjugated to aminodextran. Thereafter, aldehyde group generated from the oxidation of the sugar chain of the antibody with sodium periodate was allowed to react with the amino group of aminodextran, followed by reduction with sodium cyanoborohydride to effect covalent bond, to prepare a complex of the drug, the antibody, and aminodextran.

In Japanese Patent Application Publication JP-A3–158758 (1991), dextran was oxidized with sodium periodate; the resulting aldehyde group was allowed to react with the amino group of alkaline phosphatase and antibody, followed by reduction with sodium borohydride, to prepare a complex of the enzyme, the antibody and dextran.

In Japanese Patent Application Publication No. 6–509167 (1994), divinyl sulfone was reacted with a polymer such as dextran to introduce the vinyl group therein, followed by reaction with an enzyme and an antibody, thus a complex of the enzyme, the antibody and dextran being prepared.

All the complexes prepared by these methods were complexes formed by conjugating directly two substances to polymer. All the complexes prepared by these methods are said to show better performance, compared with direct conjugating of the two substances with no use of any carrier. However, these methods have the following drawback. More specifically, because the amount of substances capable of conjugating to a carrier in the case that two substances are to be conjugated to the carrier is finite, the larger the amount of one substance is conjugated thereto, the smaller the amount of the other substance is conjugated thereto. If the drawback can be overcome, a complex with better performance is possibly obtained.

SUMMARY OF THE INVENTION

It is thus a purpose of the invention to provide a new high quality complex of enzyme, protein and carrier, by which the aforementioned drawback can be overcome.

DETAILED DESCRIPTION OF THE INVENTION

Figure 1:
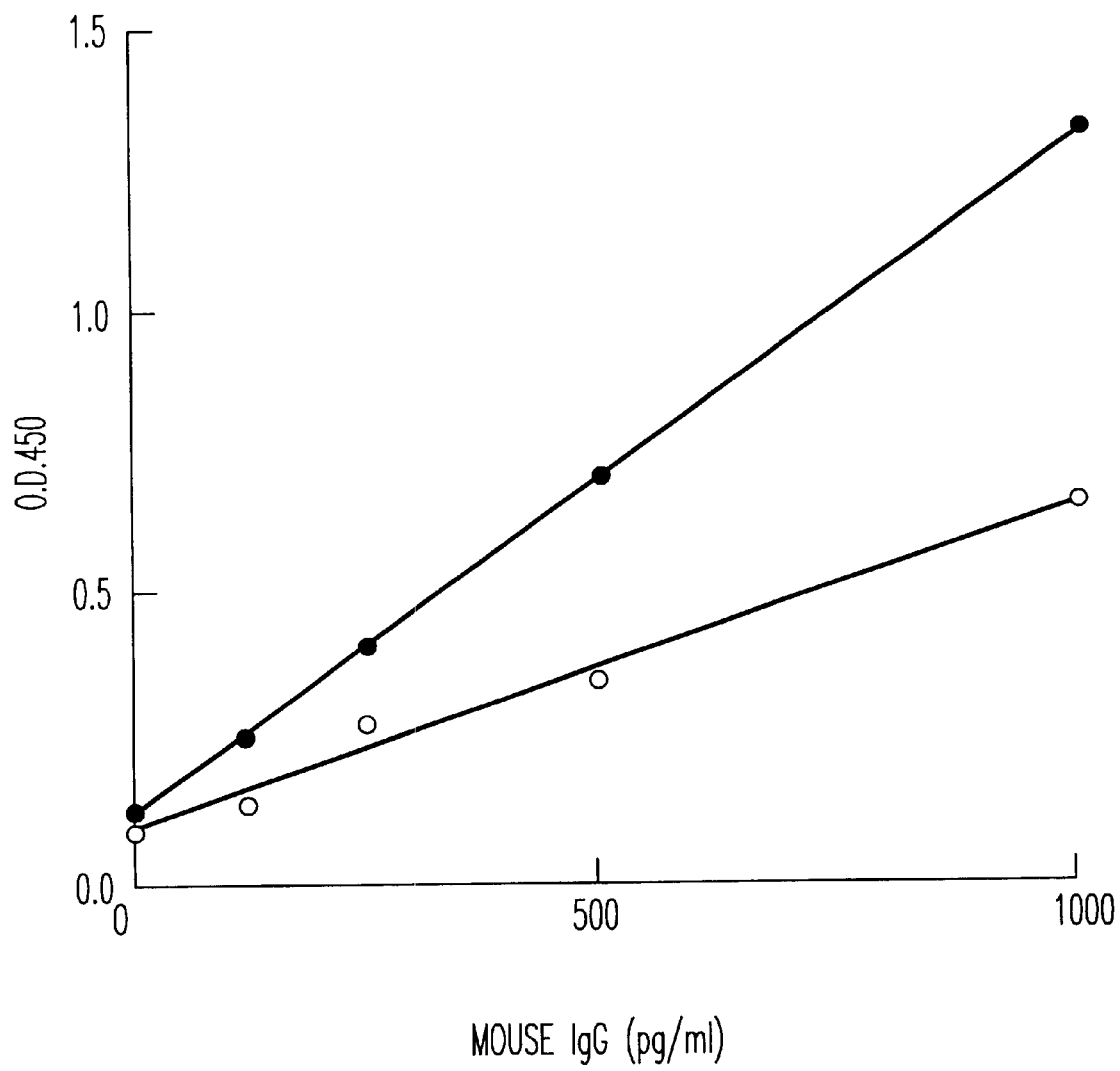
FIG. 1 shows graphs depicting the results of Example 9.

The inventors have made investigations about a method for producing a complex of enzyme, protein and carrier so as to obtain a high quality complex of enzyme, protein and carrier. The inventors have found that the purpose can be accomplished by conjugating an enzyme to a carrier and further conjugating a protein to the enzyme. After additional investigations, the invention has finally been achieved.

In other words, the invention relates to a complex of enzyme, protein and carrier prepared by conjugating two or more molecules of an enzyme to a carrier and conjugating a protein with a specific binding potency to other substance(s) to at least one molecule of the enzyme. Further, the invention relates to a complex of enzyme, protein and carrier prepared by directly conjugating, further, the same protein with a specific binding potency to other substance(s) onto the carrier of the previously prepared complex of enzyme, protein and carrier, above-mentioned. In the complex of enzyme, protein and carrier in the present invention, therefore, an enzyme and the same enzyme conjugated to a protein with a specific binding potency to other substance(s) are each conjugated numerously to a carrier; or an enzyme, the same enzyme conjugated to a protein with a specific binding potency to other substance(s) and also the same protein with a specific binding potency to other substance are each conjugated numerously to a carrier. The invention will now be described in detail hereinbelow.

The invention has been achieved during the examination of enzyme-protein complexes usable in the field of immunohistochemistry and enzyme immunoassay. However, the application of the invention to other fields is not at all limited.

The carrier referred to in accordance with the invention means proteins and polysaccharides, with no specific limitation. However, it is preferable that a great many molecules of an enzyme are conjugated to the carrier so as to raise the sensitivity of immunoassay. Therefore, (1) the molecular weight being large at a certain degree, and (2) the presence of a reactive functional group for conjugating to an enzyme or the possibility or potency of the introduction of such a reactive functional group are essential. Examples of the carrier accomplishing such purpose include peptide polymers and/or polysaccharides, appropriately with their average molecular weights of 5,000 to 500,000 Da, more preferably 10,000 to 300,000 Da, determined by gel filtration chromatography. Herein, said ranges of the molecular weights are just simple aims; molecular weights larger than the former range, with no occurrence of precipitation or sedimentation in liquid, can be used; and molecular weights smaller than the former range can also be used, provided that the purpose of the invention can be attained.

In accordance with the invention, for example, a peptide containing two or more amino groups that have binding potency is appropriately used as the carrier. One of the examples includes peptide with amino group, such as peptide comprising at least one kind of amino acid selected from the group consisting of lysine, arginine, ornithine, glutamine and other basic amino acids, these amino acids having at least one kind of amino group selected from the group consisting of $\alpha$-amino group, $\epsilon$-amino group and other amino groups. Furthermore, specific examples thereof include polylysine which is a polymer of lysine with $\epsilon$-amino group and include various peptides comprising lysine and other amino acid(s). Examples of the latter peptide polymer include random copolymer of lysine and glycine, random copolymer of lysine and serine and random copolymer of lysine and glutamic acid, which are commercially available as random copolymers with various molecular weights.

Alternatively, polysaccharides with aldehyde groups, amino groups or other active groups introduced therein can be used as the carrier of the invention as well. Examples of the polysaccharides are dextran, agarose, dextrin and soluble starch. Polysaccharides with aldehyde groups can readily be prepared by allowing polysaccharides to react with sodium periodate. Amino groups can be introduced in polysaccharides by known methods. For example, dextran with amino groups may be prepared by treating dextran with sodium periodate to generate aldehyde groups, which is allowed to react with diamine and then reduced with sodium borohydride. The introduction of active groups into polysaccharides can be carried out by known methods. For example, dextran with vinyl groups can be obtained by allowing divinyl sulfone to react with dextran.

Any of all enzymes with two or more amino groups can be used as the enzyme to be used in accordance with the invention and enzymes for general use in immunoassay are appropriately used. With no limitation, examples thereof are horse radish peroxidase, alkaline phosphatase, $\beta$-galactosidase and glucose oxidase.

The protein with a specific binding potency to other substance(s) in accordance with the invention includes (1) a protein, (2) the fragment(s) of a protein and (3) a mixture of a protein and the fragment(s) of the protein, and more practically includes an antibody capable of bonding to a specific antigen and a receptor capable of bonding to a specific ligand, such as monoclonal antibody and polyclonal antibody; avidin and streptavidin which bond specifically to biotin; Protein A and Protein G which bond specifically to antibody; lectin which bonds specifically to sugar chain; and hyaluronic acid-binding protein which bonds specifically to hyaluronic acid. Further, the protein in the invention includes protein fragments capable of bonding specifically to specific substance(s). For example, the protein fragments are antibody fragments F(ab')$_2$, Fab', and Fabc'.

The protein with a specific binding potency to other substance(s) in the present invention includes ones with a specific binding potency to other single substance and ones with a specific biding potency to other plural substances.

In accordance with the invention, first, a complex of a carrier and an enzyme is prepared. For example, a method therefor comprises modifying amino groups of a carrier into thiol groups and mixing the resulting carrier with an enzyme with maleimide group(s)modified from amino group(s). Because thiol group and maleimide group rapidly react together and make a covalent bond, the carrier conjugated with the enzyme can be prepared.

So as to introduce thiol group into the amino group of the carrier, methods using S-acetylmercaptosuccinic anhydride, n-succinimidyl 3-(2-pyridyldithio)propionate (SPDP), and S-acetylthioglycolic acid N-hydroxysuccinimide (SATA) have been known. These reagents react with amino group, so that a blocked thiol group is introduced. Thereafter, the protective group blocking the thiol group is removed by treatment with hydroxylamine in the case that S-acetylmercaptosuccinic anhydride or SATA is used, or with dithiothreitol (DTT) in the case that SPDP is used, to generate thiol group.

So as to introduce maleimide group into the amino group of the enzyme, a compound with maleimide group and succinimide ester group within one molecule is used. For example, a divalent crosslinking reagent with maleimide group at one end and with N-hydroxysuccinimide group at the other end is satisfactorily used. The examples thereof are, N-(6-maleimidocaproyloxy)succinimide (EMCS) and N-(4-maleimidobutyryloxy)succinimide (GMBS).

Other than EMCS and GMBS described above, the compounds having maleimide group and succinimide group within one molecule include those described below, with no limitation: N-succinimidyl-N-maleimidoacetate: N-succinimidyl-4-(N-maleimido)butyrate; N-succinimidyl-6-(N-maleimido)hexanoate; N-succinimidyl-4-(N-maleimidomethyl)cyclohexane-1-carboxylate: N-succinimidyl-m-(N-maleimido)benzoate; N-succinimidyl-p-(N-maleimidophenyl)-4-butyrate; N-sulfosuccinimidyl-4-(N-maleimidomethyl)cyclohexane-1-carboxylate; N-succinimidyl-m-(N-maleimido)benzoate; N-sulfosuccinimidyl-p-(N-maleimidophenyl)-4-butyrate; and the like.

Because the carrier is not required to be additionally conjugated with other substance(s) in the invention, it is preferable to prepare a complex of enzyme and carrier, in which the molecules of the enzyme are conjugated thereto as many as possible. One example of the means accomplishing the purpose is described below. A large excess of a maleimidation reagent is added to and allowed to react with the complex of enzyme and carrier, to introduce maleimide groups into almost all of the amino groups remaining on the complex. The same enzyme as used for the production of the complex is thiolated under conditions such that one or more amino groups remain on the enzyme. This is for subsequently conjugating a protein with a specific binding potency to other substance(s) by utilizing the amino group(s) remaining on the enzyme. The thus-thiolated enzyme and the complex of enzyme and carrier with maleimide groups introduced therein react together.

Subsequently, the remaining maleimide groups are blocked with a substance with thiol group. Examples of the substance with thiol group for use in blocking are mercaptoethanol, cysteamine hydrochloride and cysteine. When mercaptoethanol is used for blocking, amino group(s) is(are) present only on the thiolated enzyme of the complex of enzyme and carrier. When cysteamine hydrochloride or cysteine is used for blocking, amino groups are present on the thiolated enzyme of the complex of enzyme and carrier and on the reagent used for blocking the remaining maleimide group(s).

So as to conjugate the protein with a specific binding potency to other substance as explained previously to the complex of enzyme and carrier, the reaction of thiol group with maleimide group is satisfactorily utilized in the same manner as in the preparation of the complex of enzyme and carrier. For example, the aforementioned reagent for introducing maleimide group is allowed to react with the amino groups present on the complex of enzyme and carrier. On the other hand, the aforementioned reagent for introducing thiol group is allowed to react with the protein with a specific binding potency to other substance(s). When both of these two are mixed together, a complex of enzyme, protein with a specific binding potency to other substance(s) and carrier can be prepared. When S—S bond never involved in the binding with other substance(s) is present in the protein with a specific binding potency to other substance(s), the S—S bond is reduced with cysteamine hydrochloride or DTT, instead of thiolation, so that thiol group can be generated.

When the protein with a specific binding potency to other substance(s) has sugar chain, the sugar chain can be satisfactorily utilized. For example, it is possible that aldehyde group(s) generated by oxidizing the sugar chain of the protein with a specific binding potency to other substance(s) with sodium periodate is allowed to react with the amino group(s) on the complex of enzyme and carrier, followed by reduction to conjugate both of the two together.

The completely prepared complex is a complex where the protein with a specific binding potency to other substance(s) is conjugated onto the enzyme alone when the maleimide group(s) remaining on the carrier is(are) finally blocked with mercaptoethanol in the preparation of the complex of enzyme and carrier. The other completely prepared complex example is a complex, where the protein with a specific binding potency to other substance(s) is conjugated onto both of the enzyme and the carrier when the maleimide group(s) remaining on the carrier is (are) finally blocked with cysteamine hydrochloride or cysteine in the preparation of the complex of enzyme and carrier.

As one embodiment of the invention, the method for producing the complex of enzyme, protein and carrier using poly-L-lysine as the carrier, peroxidase as the enzyme and an antibody fragment F(ab')$_2$ as the protein with a specific binding potency to other substance is described below.

1. Preparation of thiol group-conjugated carrier

S-Acetylmercaptosuccinic anhydride is added to and allowed to react with a solution containing poly-L-lysine; thereafter, hydroxylamine is allowed to react with the resulting reaction mixture, to introduce thiol groups in the carrier (preparation of carrier-SH). Herein, the carrier is never wholly thiolated, but some of the amino groups of the carrier therein are left as they are free.

2. Preparation of maleimide group-conjugated peroxidase

EMCS is allowed to react with horse radish peroxidase (POD), to prepare maleimide group-conjugated peroxidase (M-POD).

3. Preparation of POD-poly-L-lysine complex 1

By mixing together the thiol group-conjugated carrier and M-POD and allowing them to react together, a complex (carrier-S-M-POD) is prepared. After the reaction, the remaining maleimide groups are blocked with mercaptoethanol. Through the reaction, a carrier (complex) with plural S-M-POD and SH groups introduced therein and with free amino groups can be obtained.

4. Preparation of the complex with maleimide group conjugated thereto

A large excess of an EMCS solution is added to and allowed to react with the complex obtained in 3, to introduce maleimide groups into all of the amino groups of the complex. Through the reaction, a carrier (complex) can be obtained, into which have been introduced plural S-M-POD, maleimide groups, and COOH groups generated by hydrolysis of the N-hydroxysuccinimide ester of EMCS after the binding of EMCS to the SH groups.

5. Preparation of thiol group-conjugated peroxidase

Thiol group(s) is(are) introduced into POD by allowing S-acetylthioglycolic acid-N-hydroxysuccinimide ester to react with POD and then allowing hydroxylamine to react with the resulting reaction mixture. In that case, the reactions are effected under conditions such that free amino group(s) can remain on POD (SH-POD-$NH_2$).

6. Preparation of POD-poly-L-lysine complex 2

Through the reaction of SH-POD-$NH_2$ with the complex obtained in 4, thiolated peroxidase is introduced into maleimide groups conjugated to the carrier. Subsequently, the remaining maleimide groups are treated with mercaptoethanol, to convert the remaining maleimide groups to OH groups. Through the reaction, a carrier (enzyme complex) with plural S-M-POD, plural M-S-POD-$NH_2$, COOH groups and OH groups introduced therein can be obtained.

7. Preparation of POD-poly-L-lysine complex 2 with maleimide group-conjugated POD By allowing an EMCS solution to react with the enzyme complex obtained in 6, the amino group(s) of POD in the complex is maleimidated. A complex with plural S-M-POD, plural M-S-POD-M, COOH groups, and OH groups is prepared.

8. Preparation of reduced antibody fragment

Goat anti-mouse IgG is treated with pepsin to obtain its F(ab')$_2$ fragment; and cysteamine hydrochloride is allowed to react with the F(ab')$_2$ fragment, to obtain a reduced antibody fragment (SH-Fab').

9. Preparation of a complex of enzyme, antibody and carrier

By mixing together the reduced antibody fragment and the complex obtained in 7, the antibody fragment is conjugated to the maleimide group(s) of POD. Through the reaction, a carrier (enzyme-antibody complex) conjugated with plural S-M-POD, plural M-S-POD-M-S-Fab', plural M-S-POD-M, COOH groups, and OH groups introduced therein can be obtained. If necessary, the resulting carrier may be, further, treated with mercaptoethanol, to convert the unchanged maleimide group(s) of M-S-POD-M to OH group(s), thereby the maleimide group(s) being blocked.

The complex of enzyme, protein and carrier of the invention is a first success of the realization of the aforementioned structure, and owing to the extremely large amount of the enzyme on the carrier, a strong color reaction can be effected when the enzyme is subjected to color reaction. Additionally because the protein with a specific binding potency to other substance(s) can be conjugated onto an enzyme, although many molecules of the enzyme occupy the surface of the carrier, consequently, many molecules the protein with a specific binding potency to other substance(s) can be conjugated to the complex; and thus, the capacity of the binding thereof to the other substance is extremely escalated.

Because many molecules of the protein with a specific binding potency to other substance(s) are present in the complex of enzyme, protein and carrier of the invention, even an assay subject substance of a trace amount can be captured by and bound to the complex of enzyme, protein and carrier. When the assay subject substance is conjugated to any one molecule or molecule's fragment(s) of the protein, a very strong color reaction can be effected because many molecules of the enzyme are conjugated to the complex of enzyme, protein and carrier. In accordance with the invention, in other words, even a trace amount of a substance can be detected and assayed at a high sensitivity. Thus, the invention enables accurate assay. Accordingly, an excellent assay kit can be assembled by using the complex.

For the creation of the complex of enzyme, protein and carrier in accordance with the invention, furthermore, polylysine is not first treated with EMCS (the occurrence of precipitation causes polylysine unusable) but first treated with S-acetylmercaptosuccinic anhydride to modify a part of the amino groups of the carrier to thiol groups, to which is conjugated a maleimidated enzyme, followed by treatment with a large excess of EMCS for maleimidation and carboxylation and by subsequent reaction with a thiol group-conjugated enzyme, whereby it is attained that many molecules of the enzyme can be conjugated to the carrier finally even when the number of the molecules of the enzyme conjugated is initially small, with no occurrence of precipitation or sedimentation. A marked effect can be brought about such that many molecules of the enzyme can be conjugated to the carrier in a solution state.

Accordingly, the invention brings about an excellent effect that a substance can be accurately assayed in a trace amount of a sample or in a sample diluted extremely.

EXAMPLES

So as to describe the invention in more detail, examples are described. But the invention is not limited to these examples.

Example 1

Preparation of a complex of enzyme and carrier

Maleimide group-conjugated peroxidase was prepared as follows. 20 mg of EMCS dissolved in 0.6 ml of dimethylformamide (DMF) was added to 100 mg of horse radish peroxidase dissolved in 2.4 ml of 0.1M sodium phosphate buffer, pH 7.5, for reaction at ambient temperature for 30 minutes. Thereafter, the reaction mixture was subjected to gel filtration on Sephadex G25 (manufactured by Pharmacia Co.) and the obtained filtrate was subjected to assay of the absorbance at 403 nm; a filtrate fraction with the peak at the absorbance was collected and concentrated by ultrafiltration.

Then, thiol group-conjugated polylysine was prepared as follows. 6 mg of S-acetylmercaptosuccinic anhydride dissolved in 20 μl of DMF was added to 5 mg of poly-L-lysine hydrobromide (manufactured by Sigma Co.; average molecular weight of 37,600 Da) dissolved in 1 ml of 0.1M sodium phosphate buffer, pH 6.5, for reaction at 30° C. for 20 minutes. Subsequently, 100 μl of 0.1M Tris-HCl buffer, pH 7, 10 μl of 0.1M EDTA, pH 7, and 100 μl of 1M hydroxylamine, pH 7, were added to the resulting reaction mixture, for reaction at 30° C. for 5 minutes. Then, the reaction solution was subjected to gel filtration on Sephadex G25; a filtrate fraction with the peak at the absorbance at 230 nm was collected and concentrated by ultrafiltration. In this case, all the amino groups were not modified into thiol groups.

The maleimide group-conjugated peroxidase and the thiol group-conjugated poly-L-lysine were mixed together, for reaction at 4° C. for 18 hours. A ⅒-fold volume of 0.1M mercaptoethanol was added to the resulting reaction mixture, for reaction at 30° C. for 20 minutes; thereafter, the reaction mixture was subjected to gel filtration on Ultrogel AcA44 (manufactured by Biosepla, Co.); and the absorbance of each fraction was measured at 403 nm. A complex of horse radish peroxidase and poly-L-lysine was present in a high-molecular weight filtrate fraction. The fraction was concentrated by ultrafiltration to 3 ml after the buffer was exchanged to 0.1M sodium phosphate buffer, pH 7.5. The quantity of horse radish peroxidase in the complex was 20 mg. This was designated complex 1 of enzyme and carrier.

50 mg of EMCS dissolved in 0.75 ml of DMF was added to the complex, for reaction at ambient temperature for 30 minutes. The resulting product was subjected to gel filtration on Sephadex G25; a filtrate fraction with the peak at the absorbance at 403 nm was collected and concentrated by ultrafiltration. This was designated maleimide group-conjugated complex 1 of enzyme and carrier. In this case, all the amino groups are modified into maleimide groups, while the thiol groups are converted to carboxyl groups.

Then, thiol group-conjugated horse radish peroxidase was prepared as follows.

2.5 mg of S-acetylmercaptothioglycolic acid-N-hydroxysuccinimide ester (SATA) dissolved in 0.5 ml of DMF was added to 100 mg of horse radish peroxidase dissolved in 2.5 ml of 0.1M sodium phosphate buffer, pH 7.5, for reaction at ambient temperature for 30 minutes. Thereafter, 100 µl of 0.1M EDTA, pH 7, and 0.5 ml of 1M hydroxylamine, pH 7, were added to the reaction mixture, for reaction at ambient temperature for 5 minutes. The reaction mixture was subjected to gel filtration on Sephadex G25; fractions with absorbance at 403 nm were collected and concentrated. The number of the thiol groups of the thiol group-conjugated horse radish peroxidase was assayed by the known method described in Journal of Immunoassay, 4(3), p. 209–327. Consequently, it was calculated that the number of thiol groups present in one molecule of horse radish peroxidase was 1.3. Three or more amino groups are present in one molecule of horse radish peroxidase. Thus, it was confirmed that at least one amino group remained in the thiol group-conjugated horse radish peroxidase thus prepared under the aforementioned conditions.

The maleimide group-conjugated complex 1 of enzyme and carrier and the thiol group-conjugated horse radish peroxidase were mixed together, for reaction at 4° C. for 18 hours. To the resulting product was added a ⅒-fold volume of 0.1M mercaptoethanol, for reaction at 30° C. for 20 minutes; thereafter, the resulting reaction mixture was subjected to gel filtration on Ultrogel AcA44, followed by measurement of the absorbance at 403 nm. The complex was eluted in a high-molecular weight filtrate fraction. This was designated complex 2 of enzyme and carrier.

Separately, the maleimide group-conjugated complex 1 of enzyme and carrier and the thiol group-conjugated horse radish peroxidase were mixed together, for reaction at 4° C. for 18 hours; subsequently, a ⅒-fold volume of 0.1M cysteamine hydrochloride was added to the resulting reaction mixture, followed by purification in the same manner as described above. The resulting complex was designated complex 3 of enzyme and carrier. The quantities of horse radish peroxidase conjugated of the complex 2 of enzyme and carrier and complex 3 of enzyme and carrier were 40 mg in any of them.

Example 2

Preparation 1 of a complex of enzyme, secondary antibody and carrier

The F(ab')$_2$ fragment of goat anti-mouse IgG was prepared by a known method. Goat anti-mouse IgG Fab' was prepared by the following method. 55 µl of 0.1M cysteamine hydrochloride dissolved in 0.1M sodium phosphate buffer, pH 6, containing 5 mM EDTA was added to 5 mg of goat anti-mouse IgG F(ab')$_2$ dissolved in 0.5 ml of 0.1M sodium phosphate buffer, pH 6, for reaction at 37° C. for 1.5 hours. The reaction mixture was subjected to gel filtration on Sephadex G25; a filtrate fraction with the peak at the absorbance at 280 nm was collected and concentrated by ultrafiltration.

Maleimide group-conjugated complex 2 of enzyme and carrier was prepared as follows. 10 mg of EMCS dissolved in 375 µl of DMF was added to 5 mg of the complex 2 of enzyme and carrier dissolved in 1.5 ml of 0.1M sodium phosphate buffer, pH 7.5, for reaction at ambient temperature for 30 minutes. The reaction mixture was subjected to gel filtration on Sephadex G25; and a filtrate fraction with the peak at the absorbance at 403 nm was collected and concentrated by ultrafiltration.

The maleimide group-conjugated complex 2 of enzyme and carrier and the goat anti-mouse IgG Fab' were mixed together, for reaction at 4° C. for 18 hours. After the reaction, 0.1M mercaptoethanol was added at a volume ⅒-fold the volume of the reaction solution, for reaction at 30° C. for 20 minutes; thereafter, the resulting reaction mixture was subjected to gel filtration on Ultrogel AcA44. The absorbance at 280 nm and 403 nm was measured. A high-molecular weight filtrate fraction with both the peaks was the complex of enzyme, Fab' and carrier.

Example 3

Preparation 2 of a complex of enzyme, secondary antibody and carrier

Maleimide group-conjugated complex 3 of enzyme and carrier was prepared as follows. 10 mg of EMCS dissolved in 375 µl of DMF was added to 5 mg of the complex 3 of enzyme and carrier dissolved in 1.5 ml of 0.1M sodium phosphate buffer, pH 7.5, for reaction at ambient temperature for 30 minutes. Thereafter, the reaction mixture was subjected to gel filtration on Sephadex G25; and a filtrate fraction with the peak at the absorbance at 403 nm was collected and concentrated by ultrafiltration.

The goat anti-mouse IgG Fab' prepared by the same method as described above was mixed with the maleimide group-conjugated complex 3 of enzyme and carrier, for reaction at 4° C. for 18 hours. After the reaction, 0.1M mercaptoethanol was added at a volume ⅒-fold the volume of the reaction solution, for reaction at 30° C. for 20 minutes; thereafter, the reaction mixture was subjected to gel filtration on Ultrogel AcA44. The absorbance at 280 nm and 403 nm was measured and a high-molecular weight filtrate fraction with both the peaks was the complex of enzyme, Fab' and carrier.

Example 4

Preparation 1 of a complex of enzyme, primary antibody and carrier

By a known method, rabbit anti-p53 gene product antibody (manufactured by Nichirei Corp.) was digested with pepsin, to prepare rabbit anti-p53 gene product F(ab')$_2$ fragment. The rabbit anti-p53 gene product Fab' was prepared by the following method. 55 μl of 0.1M cysteamine hydrochloride dissolved in 0.1M sodium phosphate buffer, pH 6 containing 5 mM EDTA was added to 5 mg of the rabbit anti-p53 gene product F(ab')$_2$ dissolved in 0.5 ml of 0.1M sodium phosphate buffer, pH 6, for reaction at 37° C. for 1.5 hours. The reaction was subjected to gel filtration on Sephadex G25, to collect a filtrate fraction with the peak at the absorbance at 280 nm and then concentrate the fraction by ultrafiltration. The rabbit anti-p53 gene product Fab' thus-prepared and the maleimide group-conjugated complex 3 of enzyme and carrier obtained by the same method as in Example 3 were mixed together, for reaction at 4° C. for 18 hours. After the reaction, 0.1M mercaptoethanol was added at a volume 1/10-fold the volume of the resulting reaction solution, followed by reaction at 30° C. for 20 minutes; subsequently, the reaction mixture was subjected to gel filtration on Ultrogel AcA44. The absorbance at 280 nm and 403 nm was measured; and a high-molecular weight filtrate fraction with both the peaks was complex of enzyme, Fab' and carrier.

Example 5

Preparation 2 of a complex of enzyme, primary antibody and carrier

The thiol group-conjugated anti-CD34 monoclonal antibody (manufactured by Nichirei Corp.) was prepared as follows. 0.1 mg of SATA dissolved in 50 μl of DMF was added to 5 mg of anti-CD34 monoclonal antibody dissolved in 1 ml of PBS, for reaction at ambient temperature for 30 minutes. Thereafter, 10 μl of 0.1M EDTA, pH 7, and 100 μl of 1M hydroxylamine, pH 7, were added to the resulting reaction mixture, for reaction at ambient temperature for 5 minutes. The resulting product was purified by gel filtration on Sephadex G25. The thiol group-conjugated anti-CD34 monoclonal antibody thus-prepared and the maleimide group-conjugated complex 3 of enzyme and carrier obtained by the same method as in Example 3 were mixed together, for reaction at 4° C. for 18 hours. After the reaction, 0.1M mercaptoethanol was added at a volume 1/10-fold the volume of the resulting reaction solution, followed by reaction at 30° C. for 20 minutes; subsequently, the reaction mixture was subjected to gel filtration on Ultrogel AcA44. The absorbance at 280 nm and 403 nm was measured; and a high-molecular weight filtrate fraction with both the peaks was a complex of enzyme, monoclonal antibody and carrier.

Example 6

Preparation of a complex of enzyme and streptavidin

Thiol group-conjugated streptavidin was prepared as follows. 0.25 mg of SATA dissolved in 250 μl of DMF was added to 25 mg of streptavidin dissolved in 2.5 ml of 0.1 M sodium phosphate buffer, pH 7.5, for reaction at ambient temperature for 30 minutes. Thereafter, 50 μl of 0.1M EDTA, pH 7 and 200 μl of 1M hydroxylamine, pH 7, were added to the resulting reaction mixture, for reaction at ambient temperature for 5 minutes. The resulting product was purified by gel filtration on Sephadex G25. The thiol group-conjugated streptavidin thus-prepared and the maleimide group-conjugated complex 3 of enzyme and carrier obtained by the same method as in Example 3 were mixed together, for reaction at 4° C. for 18 hours. After the reaction, 0.1M mercaptoethanol was added at a volume 1/10-fold the volume of the resulting reaction solution, followed by reaction at 30° C. for 20 minutes; subsequently, the reaction mixture was subjected to gel filtration on Ultrogel AcA44. The absorbance at 280 nm and 403 nm was measured; and a high-molecular weight filtrate fraction with both the peaks was a complex of enzyme, streptavidin and carrier.

Example 7

Comparison according to immunohistochemistry between the complex of enzyme, antibody and carrier in Example 3 and the enzyme-labeled antibody prepared by conventional method and comparison with SAB method By using anti-LCA monoclonal antibody (manufactured by Nichirei Corp.) as primary antibody, an intestinal tissue section was stained. First, a paraffin-embedded tissue was sliced in a thin section, which was deposited on a slide glass. Thereafter, treatment for paraffin removal and treatment for peroxidase removal were carried out; and the thus-prepared specimen was allowed to react with the primary antibody at ambient temperature for one hour, followed by thorough rinsing in PBS, thereby the primary antibody-bound specimen being prepared. A secondary antibody was dropwise added thereto. As the secondary antibody, was used the complex of enzyme, Fab' and carrier prepared in Example 3 at a concentration of 6 μg/ml as Fab' concentration. Separately, as the secondary antibody, the Fab' directly labeled with peroxidase by a conventional method was used at the same concentration. The labeling method by the conventional method was according to Journal of Immunoassay, 4(3), p. 209–327, wherein the materials and reagents were all identical with those in Example 3. The primary antibody of the primary antibody-bound specimen was allowed to react with the secondary antibody at ambient temperature for 30 minutes in each of the two cases above-mentioned.

In the SAB method, biotin-labeled anti-mouse polyclonal antibody (manufactured by Nichirei Corp.) was used as the secondary antibody. In this case, the primary antibody of the primary antibody-bound specimen was reacted with the secondary antibody for 10 minutes, followed by rinsing, and then received dropwise addition of peroxidase-labeled streptavidin (manufactured by Nichirei Corp.), for reaction for 5 minutes.

After, thorough rinsing was effected in each of the three cases above-mentioned; the resulting specimen received dropwise addition of a substrate solution (diaminobenzidine, hydrogen peroxide) for reaction, and then rinsed in distilled water, sealed and observed with a microscope.

The results are shown in Table 1 below. The complex of enzyme, secondary antibody and carrier prepared in Example 3 was prominently excellent, compared with the enzyme-labeled antibody prepared by the conventional method. Furthermore, the complex of enzyme, secondary antibody and carrier prepared in Example 3 was rather excellent, compared with the SAB method comprising amplification procedure.

TABLE 1

| Specimens | Intensity of staining |
|---|---|
| A | ± |
| B | +++ |
| C | + |

A: enzyme-labeled antibody by conventional method
B: the complex of enzyme, secondary antibody and carrier of Example 3
C: SAB method Example 8

Comparison according to immunohistochemistry between the complex of enzyme, primary antibody and carrier prepared in Example 4 and SAB method As the primary antibody for the SAB method, was used rabbit anti-p53 polyclonal antibody (manufactured by Nichirei Corp.) as the material in Example 4. First, a paraffin-embedded tissue of gastric cancer was sliced in a thin section and deposited on a slide glass. Thereafter, treatment for paraffin removal and treatment for peroxidase removal were carried out; and the thus-prepared specimen was allowed to react with the primary antibody at ambient temperature for one hour. After thorough rinsing in PBS, the primary antibody-bound specimen was allowed to react with biotin-labeled anti-rabbit polyclonal antibody (manufactured by Nichirei Corp.) at ambient temperature for 10 minutes. After rinsing, peroxidase-labeled streptavidin was dropwise added thereto, for reaction for 5 minutes.

Separately, the complex of enzyme, primary antibody and carrier (complex of enzyme, Fab' and carrier) prepared in Example 4 was subjected to reaction with the thus-prepared specimen as above-mentioned at ambient temperature for one hour. The concentration of the enzyme-antibody complex then was 2 µg/ml as Fab' concentration.

After thorough rinsing was effected in each of the two cases above-mentioned, the resulting specimen received dropwise addition of a substrate solution (diaminobenzidine, hydrogen peroxide) for color reaction, and then rinsed in distilled water, sealed and observed with a microscope.

As a result, the intensity of staining obtained when the complex of enzyme, primary antibody and carrier was used, was equal to the intensity obtained by the SAB method comprising amplification procedure.

Example 9

Comparison according to enzyme immunoassay between the complex of enzyme, secondary antibody and carrier prepared in Example 3 and the enzyme-labeled antibody prepared by conventional method 100 µl of goat anti-mouse IgG was added at a concentration of 10 µg/ml to a 96-well microtiter plate, for incubation at ambient temperature for 2 hours. The microtiter plate was rinsed in physiological saline, followed by addition of 200 µl of 1% bovine serum albumin, for incubation for 2 hours. 100 µl of mouse IgG at given concentrations (0 to 1,000 pg/ml) was added for incubation for 2 hours and rinsed in physiological saline. Then, to the thus-prepared microtiter plate, was added 100 µl of the complex of enzyme, secondary antibody and carrier prepared in Example 3 at a concentration of 0.5 µg/ml on an antibody quantity basis (i.e., as the antibody concentration), or 100 µl of the enzyme-labeled antibody prepared by the conventional method at a concentration of 2 µg/ml on an antibody quantity basis, for incubation for 30 minutes. The resulting microtiter plate was further rinsed in physiological saline, followed by addition of 100 µl of a substrate solution (tetramethylbenzidine, hydrogen peroxide) for reaction for 15 minutes. The reaction was terminated by adding 50 µl of 1N sulfuric acid. The degree of color reaction developed was measured by a microplate reader. As shown in FIG. 1, the results indicate that the color reaction obtained from a smaller volume of the complex of enzyme, secondary antibody and carrier prepared in Example 3 was more intense than the color reaction from the enzyme-labeled antibody prepared by the conventional method.

FIG. 1 shows the aforementioned results. In the figure, the abscissa axis expresses the concentration of mouse IgG; and the ordinate axis expresses the absorbance at 450 nm. Closed circle represents the complex of enzyme, antibody and carrier prepared in Example 3, while open circle represents the enzyme-labeled antibody prepared by the conventional method.

Advantages of the Invention

The inventive complex of enzyme, protein and carrier is useful, particularly as an enzyme-labeled antibody (as primary antibody or secondary antibody) for immunohistochemistry and enzyme immunoassay and enables immunoassay at a high sensitivity.

What is claimed is:

1. An carrier-enzyme-protein complex comprising (1) a carrier;

(2) an enzyme, two or more molecules of the enzyme being conjugated to the carrier in (1); and (3) a protein that binds to at least one substance selected from the group consisting of an antigen, an antibody, an antibody fragment, a sugar chain, hyaluronic acid and biotin, wherein said protein is conjugated to at least one molecule of the two or more molecules of the enzyme in (2) and wherein said protein is not directly conjugated to said carrier.

2. The complex of claim 1, wherein the carrier has an average molecular weight ranging from 5,000 to 500,000 Da as determined by gel filtration chromatography.

3. The complex of claim 1, wherein the carrier has an average molecular weight ranging from 10,000 to 300,000 Da as determined by gel filtration chromatography.

4. The complex of claim 1, wherein the carrier has two or more amino groups.

5. The complex of claim 1, wherein the carrier is selected from the group consisting of (a) a peptide polymer having two or more basic amino groups and (b) a polysaccharide having one or more introduced active groups, wherein the active group(s) are selected from the group consisting of an amino group, an aldehyde group and a vinyl group.

6. The complex of claim 1, wherein the carrier comprises a peptide polymer having two or more amino groups.

7. The complex of claim 1, wherein the carrier comprises polylysine.

8. The complex of claim 1, wherein the carrier comprises a polysaccharide comprising one or more aldehyde group(s).

9. The complex of claim 1, wherein the carrier comprises a polysaccharide comprising one or more amino group(s).

10. The complex of claim 1, wherein the carrier comprises a polysaccharide comprising one or more vinyl group(s).

11. The complex of claim 1, wherein the enzyme comprises horse radish peroxidase.

12. The complex of claim 1, wherein the enzyme comprises alkaline phosphatase.

13. The complex of claim 1, wherein the enzyme comprises β-galactosidase.

14. The complex of claim 1, wherein the enzyme comprises glucose oxidase peroxidase.

15. The complex of claim 1, wherein the protein comprises an antigen.

16. The complex of claim 1, wherein the protein comprises an antibody or an antibody fragment.

17. The complex of claim 1, wherein the protein comprises a polyclonal antibody or a monoclonal antibody.

18. The complex of claim 1, wherein the protein comprises at least one antibody fragment selected from the group consisting of F(ab')$_2$, Fab' and Fabc'.

19. The complex of claim 1 wherein the protein comprises a protein that binds to a sugar chain.

20. The complex of claim 1, wherein the protein comprises a protein that binds to hyaluronic acid.

21. The complex of claim 1, wherein the protein comprises a protein that binds to biotin.

22. The complex of claim 1 wherein the protein comprises avidin or streptavidin.

23. An immunoassay kit comprising the complex of claim 1.

24. The immunoassay kit of claim 23, wherein said kit is immunohistostaining or enzyme immunoassay, or both.

25. A method for detecting a substance comprising:
contacting the carrier-enzyme-protein complex of claim 1 with a sample suspected of containing a substance that binds to the protein in said complex, and
determining the amount of binding.

26. The method of claim 25, wherein said carrier-enzyme-protein complex is contacted with a tissue sample under conditions suitable for immunohistostaining.

27. The method of claim 25, wherein said carrier-enzyme-protein complex is contacted with a sample under conditions suitable for an enzyme immunoassay.

* * * * *